(12) United States Patent
Kim et al.

(10) Patent No.: US 8,431,337 B2
(45) Date of Patent: Apr. 30, 2013

(54) APPARATUS FOR DETECTING NUCLEIC ACIDS USING BEAD AND NANOPORE

(75) Inventors: Kui Hyun Kim, Daejeon-si (KR); Jun Hong Min, Yongin-si (KR); Ah Gi Kim, Yongin-si (KR); In Ho Lee, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 1239 days.

(21) Appl. No.: 11/499,052

(22) Filed: Aug. 4, 2006

(65) Prior Publication Data

US 2010/0267011 A1 Oct. 21, 2010

(30) Foreign Application Priority Data

Aug. 4, 2005 (KR) .................. 10-2005-0071344

(51) Int. Cl.
*C12Q 1/68* (2006.01)
*C12Q 1/00* (2006.01)
*C12M 1/34* (2006.01)

(52) U.S. Cl.
USPC ... 435/6.1; 435/283.1; 435/287.2; 422/82.01; 204/403.06

(58) Field of Classification Search .................. None
See application file for complete search history.

(56) References Cited

U.S. PATENT DOCUMENTS

| | | | |
|---|---|---|---|
| 6,015,714 A | 1/2000 | Baldarelli et al. | |
| 6,284,525 B1 | 9/2001 | Mathies et al. | |
| 6,362,002 B1 | 3/2002 | Denison et al. | |
| 6,428,959 B1 | 8/2002 | Deamer | 435/6 |
| 6,616,895 B2 | 9/2003 | Dugas et al. | |
| 6,720,187 B2 | 4/2004 | Bedingham et al. | |
| 6,861,221 B2 | 3/2005 | Mirkin et al. | |
| 6,936,433 B2 * | 8/2005 | Akeson et al. | 435/23 |
| 7,468,271 B2 | 12/2008 | Golovchenko et al. | |
| 7,851,203 B2 * | 12/2010 | Letant et al. | 435/287.2 |
| 2002/0086307 A1 | 7/2002 | Amin et al. | |
| 2002/0094526 A1 * | 7/2002 | Bayley et al. | 435/6 |
| 2002/0160381 A1 | 10/2002 | Mirkin et al. | |
| 2003/0104428 A1 | 6/2003 | Branton et al. | 435/6 |
| 2004/0038260 A1 | 2/2004 | Martin et al. | |
| 2004/0142285 A1 | 7/2004 | Jung et al. | |
| 2004/0144658 A1 | 7/2004 | Flory | 205/777.5 |
| 2005/0059169 A1 | 3/2005 | Hattori | |
| 2005/0136408 A1 * | 6/2005 | Tom-Moy et al. | 435/6 |

(Continued)

OTHER PUBLICATIONS

Chang et al., "DNA-Mediated Fluctuations in Ionic Current through Silicon Oxide Nanopore Channels," Nano Letters, 4 (8): 1551-1556 (2004).

(Continued)

*Primary Examiner* — Betty Forman
(74) *Attorney, Agent, or Firm* — Cantor Colburn LLP

(57) ABSTRACT

There are provided a method and apparatus for detecting nucleic acid using bead and nanopore, and more specifically, a method and apparatus capable of detecting nucleic acid fragments of 70 bps to 300 bps in length by a nanopore detection unit with nanopores of 20 to 120 nm in diameter by attaching a bead to a nucleic acid probe and then detecting the bead attached to nucleic acid not nucleic acid itself. Accordingly, the present invention can detect the nucleic acid fragments using the nanopore detection unit with nanopores of 20 to 120 nm in diameter, even in case where Polymerase Chain Reaction (PCR) products are given as the sample, particularly the PCR products are the nucleic acid fragments of 70 to 300 bps in length.

6 Claims, 4 Drawing Sheets

U.S. PATENT DOCUMENTS

| | | | |
|---|---|---|---|
| 2005/0227235 A1* | 10/2005 | Carr et al. | 435/6 |
| 2005/0227239 A1 | 10/2005 | Joyce | |
| 2006/0210995 A1* | 9/2006 | Joyce | 435/6 |
| 2006/0275778 A1* | 12/2006 | Wu et al. | 435/6 |
| 2007/0218471 A1* | 9/2007 | Kim et al. | 435/6 |

OTHER PUBLICATIONS

Chen, et al., "Probing Singe DNA Molecule Transport Using Fabricated Nanopores," Nano Letters, 4(11): 2293-2298 (2004).

Matsumoto et al., "Flow-Through-Type DNA Array Based on Ideally Ordered Anodic Porous Alumina Substrate," Adv. Mat., 16: 23-24 (2004).

Restriction Requirement dated Nov. 2, 2007 for U.S. Appl. No. 11/550,099.

Response to Restriction Requirement filed Nov. 29, 2007 for U.S. Appl. No. 11/550,099.

Non-Final Office Action dated Feb. 1, 2008 for U.S. Appl. No. 11/550,099.

Response to Non-Final Office Action filed Apr. 30, 2008 for U.S. Appl. No. 11/550,099.

Final Office Action dated Aug. 1, 2008 for U.S. Appl. No. 11/550,099.

Response to Final Office Action filed Oct. 31, 2008 for U.S. Appl. No. 11/550,099.

Advisory Action dated Dec. 5, 2008 for U.S. Appl. No. 11/550,099.

Response to Advisory Action filed Jan. 30, 2009 for U.S. Appl. No. 11/550,099.

Non-Final Office Action dated Apr. 14, 2009 for U.S. Appl. No. 11/550,099.

Response to Non-Final Office Action filed Jul. 13, 2009 for U.S. Appl. No. 11/550,099.

Final Office Action dated Nov. 19, 2009 for U.S. Appl. No. 11/550,099.

Response to Final Office Action filed Jan. 19, 2010 for U.S. Appl. No. 11/550,099.

Non-Final Office Action dated Jul. 8, 2010 for U.S. Appl. No. 11/550,099.

Response to Non-Final Office Action filed Oct. 5, 2010 for U.S. Appl. No. 11/550,099.

Supplemental Amendment filed Nov. 22, 2010 for U.S. Appl. No. 11/550,099.

Final Office Action Dated Dec. 15, 2010.

Saleh, O.A. et al., Direct detection of antibody-antigen binding using an on-chip artificial pore, Proc Natl Acad Sci USA., 2003; 100(3): 820-824.

Zanchet, D. et al., Electrophoretic and Structural Studies of DNA-Directed Au Nanoparticle Groupings, J. Phys. Chem. B. 2002; 106:11758-11763.

* cited by examiner

- Streptococcus pneumoniae

- Bordetella pertusis

- Staphylococcus aureus

- Klebsiella pneumoniae

APPARATUS FOR DETECTING NUCLEIC ACIDS USING BEAD AND NANOPORE

FIELD OF THE INVENTION

The present invention generally relates to a method and apparatus for detecting nucleic acids using nanopore, and more specifically, to a method and apparatus capable of detecting nucleic acid fragments of 70 bps to 300 bps in length through the use of a nanopore detection unit with nanopores of 20 to 120 nm in diameter by allowing a bead not nucleic acids to be detected through attachment of the bead to a nucleic acid probe.

BACKGROUND OF THE INVENTION

A variety of methods for detecting target biomolecule in a sample have been developed. Among those methods, the method using nanopore is a bio-pore imitation system, which is in the spotlight as a DNA detection system with high-sensitivity and also as a sequencing tool in the future.

There are many DNA detection systems using the nanopore. For example, U.S. Pat. No. 6,428,959 discloses methods of determining the presence of double stranded nucleic acids in a fluid sample by measuring, while translocating nucleic acids in the sample through a nanopore, an amplitude of current flowing through the nanopore and then blockading the current.

U.S. Patent Application Publication No. 2004/0144658 describes an apparatus and method for biopolymer identification during translocation through a nanopore, which detects a translocating biopolymer with a nanopore based on the concept that in case where a bias potential is ramped across both electrodes, the increase of current passing over a barrier occurs when the carrier energy sequentially matches with the conduction band energies of the translocating biopolymer.

U.S. Patent Application Publication No. 2003/0104428 provides a method for characterization of nucleic acid molecules, in which a greater signal change is accomplished by the modification of specific local area using a protein specific to a nucleotide sequence. This publication discloses a technique of detecting DNA with a specific sequence using nanopores.

However, these conventional methods and apparatuses for detecting DNA using nanopores have problems in that DNA to be detected must have the specific sequence or the structure of apparatuses and the condition for detection are complex, thus rendering the manufacturing process very complicated.

Many efforts have been made to provide nanopores having such a small diameter as bio-pore up to date. In actual, however, the manufacture thereof is quite difficult; and accordingly, a need has existed for a method capable of detecting nucleic acid fragments below 2,000 bps using a nanopore sensor with a diameter ranging from 20 to 120 nm.

SUMMARY OF THE INVENTION

While the inventors of the present invention were researching new methods for detecting nucleic acids using a nanopore to solve the problems of the prior art, we found that nucleic acid fragment can be detected by a nanopore detection unit with nanopores of 20 to 120 nm in diameter to a high-sensitivity by attaching a bead to a nucleic acid and then detecting the bead not nucleic acid, even in case where there is given as a sample Polymerase Chain Reaction (PCR) product, particularly PCR product of nucleic acid fragment of 70 bps to 300 bps in length.

Therefore, a primary object of the present invention is to provide a method and apparatus for detecting nucleic acids in a sample by detecting the bead attached to nucleic acid not nucleic acid itself in the sample through the use of a nanopore detection unit, even in case where the diameter of nanopores ranges from 20 to 120 nm.

Another object of the present invention is to offer a method and apparatus for detecting nucleic acids in PCR products using a nanopore detection unit with nanopores of 20 to 120 nm in diameter, even in case where the sample to be detected is the PCR products.

Still another object of the present invention is to provide a method and apparatus for detecting nucleic acid in PCR products employing a nanopore detection unit with nanopores of 20 to 120 nm in diameter, even in case where the PCR products are nucleic acid fragments of 70 to 300 bps in length.

BRIEF DESCRIPTION OF DRAWINGS

The above and other objects and features of the instant invention will become apparent from the following description of preferred embodiments taken in conjunction with the accompanying drawings, in which.

DETAILED DESCRIPTION OF THE PRESENT INVENTION

Figure 1:
FIG. 1 shows a waveform diagram of current measured when 1 M KCl solution without bead is passed through after applying 300 mV to a nanopore detection unit with nanopores of 100 nm in diameter.

The other objectives and advantages of the invention will be understood by the following description and will also be appreciated by the examples of the invention more clearly. Further, the objectives and advantages of the invention will readily be seen that they can be realized by the means and its combination specified in the claims.

To accomplish the above object of the present invention, there is provided a method of detecting nucleic acids using bead and nanopore, the method comprising the steps of: preparing nucleic acid probes, each of which contains an artificial sequence cleavable by a specific enzyme within the sequence complementary to a target nucleic acid; preparing bead-bonded nucleic acid probes by attaching beads to the prepared nucleic acid probes; fixing the bead-bonded nucleic acid probes to the surroundings of the nanopores of a solid substrate having nano-sized pores; adding a sample containing target nucleic acids to the solid substrate to which the nucleic acid probes are fixed and hybridizing the target nucleic acids with the nucleic acid probes; allowing the specific enzyme to react on the solid substrate in which the target nucleic acids are hybridized with the nucleic acid probes to produce nucleic acid fragment-bonded beads as enzyme reaction products; and detecting an electric signal generated when the nucleic acid fragment-bound beads contained in the enzyme reaction products pass through the nanopores.

The term "nucleic acid probe" used herein refers to a single stranded oligonucleotide of which sequence is known. The probe can be artificially designed to contain a sequence cleavable by a specific enzyme which can specifically act on the sequence within the range of sequence complementary to a target nucleic acid. It is also preferred to have a structure to which a bead may be easily attached. As one example of the artificial sequence cleavable by the specific enzyme included in the nucleic acid probe, it may be implemented with a mismatched sequence in which the sequence has 1 to 3 bases mismatched with the target nucleic acid. Due to the merit of facilitating the implementation, the mismatched sequence may be frequently used; and in this case, a mismatch cleavage enzyme is used as the specific enzyme.

Meanwhile, the term "enzyme" used herein should be understood as a wide concept which involves not only biomaterials but also cleavable chemicals which may act on the sequence artificially designed in the nucleic acid probe, that is, chemicals which may act on a specific sequence and structure merely.

And also, a variety of methods may be used to attach beads to the nucleic acid probes prepared. For example, avidin-biotin reaction may be adopted which is a typical example of protein-ligand reactions. In this method, there are first prepared the followings: the nucleic acid probe to which the biotin is bonded and which includes the oligonucletide with sequence on which an enzyme may act, and the bead which is a conjugate (for example, streptavidin-Au conjugate) of avidin and different metal. The bead-bonded nucleic acid probe is formed by occurring avidin-biotin reaction when the nucleic acid probe contacts with the conjugate of avidin-metal. Although concrete examples are not disclosed herein, it will be understood by those skilled in the art that a variety of nucleic acid probes to which beads are attached can be prepared to employ in the present invention through the use of various methods well known in the art.

Next, the nucleic acid probe to which the bead is attached is fixed to the surroundings of nanopores of a solid substrate having nano-sized pores by the methods well known in the art. In some cases, the bead-bonded nucleic acid probe may be prepared by first fixing the nucleic acid probe to the surroundings of nanopores of the solid substrate using a known method and then attaching the bead to the fixed nucleic acid probe.

Thereafter, added to the solid substrate to which the bead-bonded nucleic acid probes are fixed is a sample of fluid state to be analyzed, wherein the sample contains, as a target material, single-stranded nucleic acids with the sequence complementary to the bead-bonded nucleic acid probe, particularly DNA or RNA.

Therefore, a hybridization reaction occurs between the bead-bonded nucleic acid probes fixed to the solid substrate and the target material contained in the sample.

Next, owing to the specific enzyme added to the solid substrate, the cleavable part of the sequence included in the hybridized nucleic acid is digested, resulting in the release of bead (i.e., nucleic acid fragment-bonded bead) to which a nucleic acid fragment is attached as an enzyme reaction product. Since an electric signal generated during the translocation of the nucleic acid fragment-bonded beads through nanopores of the solid substrate is detected, it is very easy to detect whether or not the nucleic acid fragment exists in the enzyme reaction product by detecting the nucleic acid fragment-bonded beads in the enzyme reaction product.

Figure 2:
FIG. 2 presents a waveform diagram of current measured when 1 M KCl solution in the presence of streptavidin-Au conjugate of 5 nm in diameter with a density of 5 ug/ml is passed through by the nanopore detection unit under the same condition as that of FIG. 1.

It is apparent from the observation that while no current amplitude occurs when a fluid without the use of beads, i.e., only 1 M KCl solution is translocated through the nanopore detection unit as shown in FIG. 1, the current amplitude takes place when 1 M KCl solution in the presence of streptavidin-Au conjugate of 5 nm in diameter with a density of 5 ug/ml is dissolved and translocated as shown in FIG. 2.

On the other hand, the sample and specific enzyme added to the solid substrate are provided as a fluid state dissolved in a solvent which is electrically conductive. As examples of the solvent, there may be used any convenient solvent that is electrically conductive. The solvent may be aqueous solvent such as pure water or water to which one or more additives, for example, buffer, salt (e.g., potassium chloride) are added. The pH of the fluid sample is typically about pH 6.0 to 9.0, more preferably about pH 7.0 to 8.5.

Figure 3:
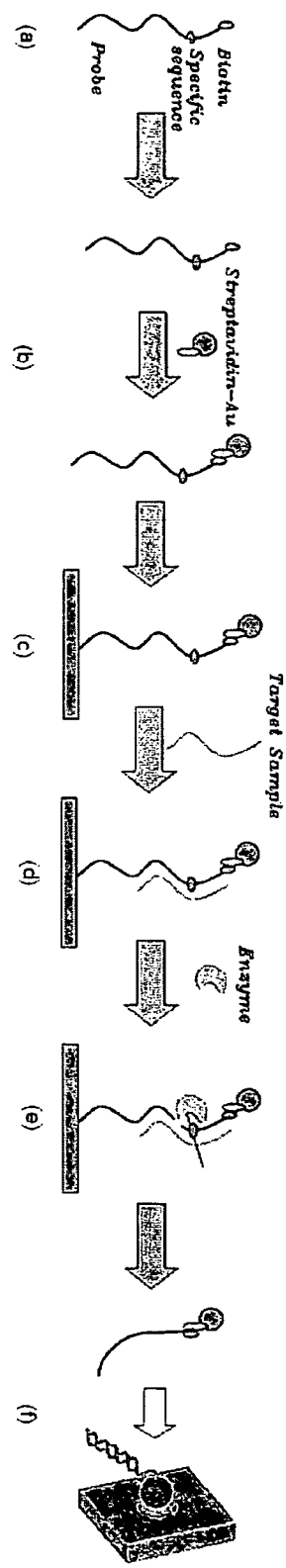
FIG. 3 is a schematic diagram briefly showing a nucleic acid detecting method using bead and nanopore in accordance with the present invention.

Referring to FIG. 3 schematically showing the method for detecting nucleic acid fragments using bead and nanopore according to the present invention, the nucleic acid fragments can be detected by conducting the following steps of: (a) preparing an oligonucleotide probe to which a sequence cleavable by a specific enzyme and biotin are attached; (b) attaching a bead, i.e., streptavidin-Au conjugate to the probe by an avidin-biotin reaction; (c) fixing the bead-bonded nucleic acid probe to a solid substrate; (d) hybridizing the bead-bonded nucleic acid probe with a target nucleic acid in a fluid sample; (e) adding a specific enzyme to the solid substrate to digest the specific sequence contained in the nucleic acid probe; and (f) translocating the enzyme reaction product including the nucleic acid fragment-bonded bead through nanopores of a nanopore detection unit.

In accordance with the present invention, as mentioned above, the bead is attached to the nucleic acid probe with the artificial sequence cleavable by the specific enzyme and the sample including the target nucleic acid is added to the solid substrate to which the bead-bonded nucleic acid probe is fixed. And then, after the bead-bonded nucleic acid probe and the target nucleic acid are hybridized, an enzyme specific to the artificial sequence is added to the solid substrate so that the artificial sequence is digested. As a result of this, the nucleic acid fragment-bonded bead is presented in the enzyme reaction product; and therefore, the bead attached to the nucleic acid fragment causes the current amplitude to be increased during the translocation of the nucleic acid fragments through nanopores, thereby detecting the nucleic acid fragments to a high-sensitivity. Specifically, the volume of the bead-bonded nucleic acid is increased compared to the bead-free nucleic acids, which in turn leads to the increase of the current amplitude. This can be seen from the following equation:

$$I_{block} = \rho \times A \times V_{bias} / L_{pore}$$

wherein $I_{block}$ is a blocking current, $\rho$ is a conductivity of solution, $V_{bias}$ is an applied voltage, $L_{pore}$ is an effective length of pore, and A is a sectional area of moving molecule.

Therefore, the conductivity of solution may be first increased in order to increase the blocking current. But, this causes the increase of noise as well as the increase of signal. Alternatively, the applied voltage may be increased, but noise problem is also introduced. Further, the length of nanopore may be decreased, but the length is increased in the case of channel-type pore. Under the circumstances, it may be efficient to increase the sectional area of moving molecule in order to increase the blocking current. In view of the foregoing, the present invention is implemented in such a way that the bead is attached to the nucleic acid to increase the sectional area of moving molecule simultaneously while reducing the length of nucleic acid fragments.

The nanopore used in the method of the present invention is characterized by 20 nm to 120 nm in diameter. The nanopore implies a structure having channel or pore (opening) of which diameter is at a nano-scale, and is a part of a namapore detection unit of known technical construction including a nanopore sensor. In the present invention, the construction of the apparatus and the method for detecting nucleic acid fragments using the nanopore are the same as those of the conventional techniques except that the present invention uses the bead and thus makes it possible to use required nanopores of 20 nm to 120 nm in diameter.

In other words, the nanopore detection unit generally applies an electric field through an array of nanopores arranged in plural and monitors the change of the current amplitude through the nanopores, so that the target material in the fluid translocated through the nanopores can be detected. The current amplitude through nanopores is monitored during the movement of fluid and the change of the current amplitude is related to the passage of the target material through the nanopres; and thus, the target material can be efficiently detected from the value of current amplitude measured.

The bead used in the method of the present invention is characterized by 1 nm to 10 nm in size.

In one specific embodiment to concretely implement the method of the present invention, the streptavidin-Au conjugate with a size of 5 nm was used as the bead. Besides, various kinds of beads may be used as long as they are attachable to the nucleic acid probe and sized to be supported by the probe. When the size of the bead is less than 1 nm, the nanopore may not detect the bead; and when the size of bead is greater than 10 nm, the bead may not be supported by the probe and also there may be a concern that the apparatus to perform the method become too enlarged. Therefore, it is preferred to use the bead with a size of 1 nm to 10 nm. In the aspect of the size of the apparatus and the ability of the nucleic acid probe to support the bead, it is more preferred to allow the bead used in the method of the present invention to have a size of nm or less. It is understood that if the bead with a size of less than 1 nm is to be utilized according to the advance of technique, the apparatus to perform the method of the present invention may be remarkably sophisticated.

The sample used in the method of the present invention is characterized by PCR product. Generally, most of PCR products have a size of 1 to 2 kbs or less; and therefore, it is difficult to detect such nucleic acids of the PCR product itself as the sample through the currently known nanopore detection unit. But, since the present invention detects the bead attached to the nucleic acid fragment not nucleic acid, the nucleic acid itself is not required to have a big size and thus DNA or RNA fragments amplified by PCR reaction can be detected by performing the method of the present invention. According to the method of the present invention, therefore, it can be very easily confirmed whether the production of the desired DNA or RNA is made by the PCR method.

Furthermore, the method of the present invention is more useful because it can be also used, even in case where the PCR product is DNA or RNA fragments of 70 bps to 300 bps.

In another aspect, there is provided an apparatus for detecting nucleic acid fragment-bonded beads translocated through nanopores, the apparatus comprising: a nanopore detection unit, which includes (a) a solid substrate having nanopores of the size allowing nucleic acids to be translocated through, (b) electrodes applying a voltage to the nanopores of the solid substrate, and (c) nucleic acid probes to which beads are attached, wherein each probe has an artificial sequence cleavable by a specific enzyme within the sequence complementary to a target nucleic acid and is fixed to the surroundings of the nanopores of the solid substrate; a sample storage chamber for storing the sample containing the target nucleic acids to be added to the nanopore detection unit; and an enzyme storage chamber for keeping the specific enzyme to be added to the nanopore detection unit.

Figure 4:
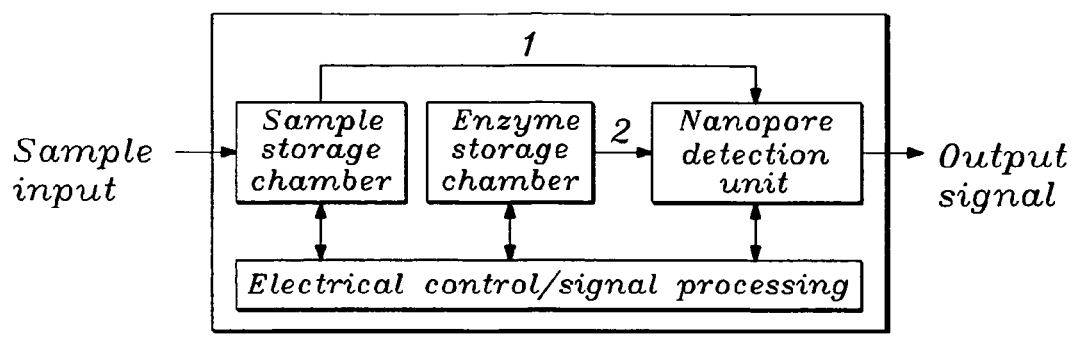
FIG. 4 exemplifies functional elements of a nucleic acid detecting apparatus in accordance with the present invention.

Referring to FIG. 4 that shows functional elements of the nucleic acid detecting apparatus of the present invention that detects beads, to which nucleic acid fragments are attached, translocated through nanophores, the apparatus broadly comprises the three functional elements of a sample storage chamber, an enzyme storage chamber and a nanopore detection unit. Although not shown in FIG. 4, it can be seen that the apparatus further comprises a connection part for joining the functional elements. It is preferred that the connection part is a channel with a diameter permitting the translocation of the bead.

The nanopore detection unit in the apparatus for detecting nucleic acids according to the present invention is an electronic unit which includes a solid substrate with nanopores and electrodes for applying a voltage to the nanopores of the solid substrate, like the commonly known nanopore sensor. The unit detects a target material contained in a fluid sample by monitoring the change of current amplitude observed during the translocation of the sample through the nanopores. The technical constitution of the nanopore detection unit of the present invention differs from that of the known nanopore sensor in that the inventive unit uses the nanopores with a diameter ranging from 20 nm to 120 nm. In addition, the nanopore detection unit of the present invention is considerably distinguished from the known nanopore sensor in that the unit of the present invention further includes, as its technical element, the bead-bonded nucleic acid probe fixed to the surroundings of nanopores to detect nucleic acid fragments contained in the fluid translocated through the nanopores, while utilizing the nanopores with a diameter of 20 nm to 120 nm.

The bead-bonded nucleic acid probe must contain an artificial sequence which is cleavable by a specific enzyme within the sequence complementary to the target nucleic acid. Due to easy implementation, the cleavable artificial sequence is frequently used in the form of mismatched sequence with 1 to 3 bases which is mismatched with the target nucleic acid involved in a sample. Also, the nucleic acid probe can be changed depending on the sample to be detected in the sample storage chamber. The bead attached to the nucleic acid probe was already described above; and therefore, details thereof will be omitted here.

The sample storage chamber of the present invention is used to retain the sample having the target nucleic acid. The sample may be PCR product, i.e., fluid material including the target nucleic acid of DNA or RNA fragments amplified by PCR reaction, wherein, in particular, the target nucleic acid may be DNA or RNA fragment of 70 bps to 300 bps in length. It may be implemented in such a way that the sample storage chamber keeps the sample injected from the outside. Alternatively, it may be implemented in such a manner that the chamber stores the sample after producing a desired sample by a known PCR chip where necessary.

The enzyme storage chamber of the present invention retains the specific enzyme to produce the nucleic acid fragment-bonded bead as an enzyme reaction product, in which the enzyme digests the cleavable sequence part included in the hybridized nucleic acid produced from the hybridization reaction between the bead-bonded nucleic acid probe fixed to the solid substrate of the nanophore detection unit and the target nucleic acid contained in the sample. Especially, in case where the cleavable sequence is the mismatched sequence with 1 to 3 bases mismatched with the target nucleic acid, the specific enzyme is a mismatch cleavage enzyme. It may be implemented in such a way that the enzyme storage chamber keeps the specific enzyme injected from the outside or keeps the enzyme after producing a desired enzyme, according to the advance of technique, where necessary.

Meanwhile, although there is not specifically described, each functional element of the present invention can be implemented on a process-on-a-chip or lab-on-a-chip using Microfluidic unit or MEMS device known in the art. The Microfluidic unit generally includes a connection part to join each of the sample storage chamber and the enzyme storage chamber to the nanopore detection unit, a control part that is formed between the nanopore detection unit and the sample storage chamber and between the enzyme storage chamber and the nanopore detection unit and controls an opening/closing operation in response to a corresponding specific signal, and a driving part that provides a driving power to move the fluid sample from the sample storage chamber and the enzyme from the enzyme storage chamber to the nanopore detection unit and translocate the enzyme reaction product produced by the nanopore detection unit. Specifically, the connection part used for the present invention in the known Microfluidic unit is preferably a microchannel with a diameter through which the bead may be passed, the control part is preferably a flap valve which is a kind of active value and controls the flow of fluid by opening or closing the flap by the driving power, and the driving part is preferably a micropump.

Hereinafter, the present invention will be described in more detail in the following examples. The following examples are provided to exemplify the present invention merely; and therefore, it should be interpreted not to limit the scope of the present invention by these examples.

Experiment 1

Determination of the Change of Current by the Nanopore Detection Unit without Bead A current was measured through the nanopore detection unit containing the arrays of nanopores with a diameter of 100 nm using only the conductive fluid medium without bead. The conductive fluid medium was 1 M KCl and a voltage of 300 mV was applied to the nanopore detection unit. FIG. 1 shows a waveform diagram of current measured when only the conductivity fluid is passed through the nanopore detection unit without bead. As shown in FIG. 1, it could be seen that there was little current change when only the conductive fluid was used without bead.

Experiment 2

Determination of the Change of Current by the Nanopore Detection Unit with Bead

A current was measured through the nanopore detection unit containing the arrays of nanopores with a diameter of 100 nm using the conductive fluid medium to which beads were added. The beads were streptavidin-Au conjugates with a diameter of 5 nm, the conductive fluid medium was 1 M KCl to which beads were added with a density of 5 ug/ml, and a voltage of 300 mV was applied to the nanopore detection unit. FIG. 2 presents a waveform diagram of current measured when the conductivity fluid containing the beads is passed through the nanopore detection unit. As presented in FIG. 2, it could be seen that there was a remarkable change in current when the conductive fluid with beads was used.

EXAMPLE

Detection of Bead-Bonded Nucleic Acid Fragments

In Experiments 1 and 2, it was confirmed that the beads could be detected by the nanopore detection unit containing nanopores with a diameter of 100 nm. To detect the sample of 1 kps or less, more preferably nucleic acid fragments of PCR products of 70 to 300 bps through the nanopore detection unit containing nanopores with a diameter of 100 nm, using the method illustrated in FIG. 3 and the apparatus illustrated in FIG. 4, the following steps were carried out.

a. Step 1: Preparation of Nucleic Acid Probe with the Structure which Includes the Sequence Cleavable by a Specific Enzyme and Facilitates the Attachment of Bead The target nucleic acid was first decided as $E.\ coli$ BL21 16s RNA. Next, there was prepared, as the nucleic acid probe, 80 uM of 60 mer oligonucleotide including 25 mer oligonucleotide probe (AAAGTACTTTCAACGGGGAG-GAAGG) which is hybridized with the nucleic acid fragment together with 1 to 3 bases mismatched with the target nucleic acid in the sequence, and nonspecific sequence of 17 mer (poly T) at the 5' end and 18 mer (poly T) at the 3' end on the basis of the 25 mer. The amine at the 5' end of the 60 mer oligonucleotide was modified and the biotin was attached to the 3' end of the 60 mer oligonucleotide.

b. Step 2: Attachment of Bead to the Nucleic Acid Probe Prepared in Step 1

The biotin-bonded nucleic acid probe prepared in step 1 was contacted with 5 ug/ml of streptavidin-Au conjugate wherein the reaction of avidin-biotin was brought out at the room temperature for 30 minutes. Thus, the bead-bonded nucleic acid probe was prepared.

c. Step 3: Fixation of the Bead-Bonded Nucleic Acid Probes Prepared in Step 2

Figure 5:
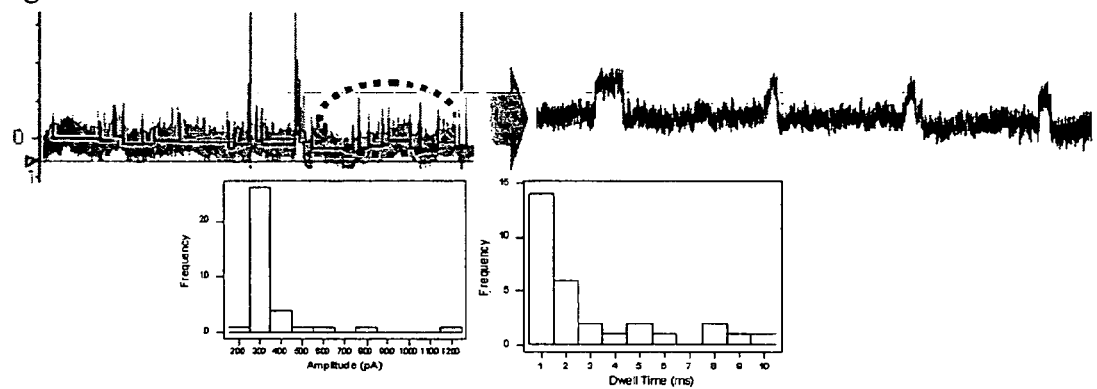
FIG. 5 depicts a waveform diagram of current measured after carrying out the steps of FIG. 3 with the apparatus of FIG. 4, using as a target material the PCR product of *E. coli* BL21 16s RNA which is hybridized with the nucleic acid probe shown in FIG. 3, followed by particularly applying a voltage of 300 mV to the nanopore detection unit.

80 uM of the bead-bonded nucleic acid probes prepared in step 2 were immobilized on the surroundings of nanopores of the solid substrate constituting the nanopore detection unit using 9 mM PEG 10000 in 25 mM.

d. Step 4: Hybridization of a Sample Containing Nucleic Acids with the Nucleic Acid Probes Fixed to the Surroundings of Nanopores of the Solid Substrate $E.\ coli$ BL21 16s RNA was first amplified by PCR reaction well known in the art. Next, after the denaturation of the amplified product to make the product single-stranded, 70 bps DNA with the sequence complementary to the nucleic acid probe was prepared. Subsequently, 40 nM of the sample was added to the surroundings of nanopores of the solid substrate and the mixture was incubated at 37° C. for about 1 hour to hybridize the target material contained in the sample with the bead-bonded nucleic acid probes. Finally, the remaining fluid was removed.

e. Step 5: Digestion of the Mismatched Sequence of the Hybridized DNA with Enzyme Added to the surroundings of nanopores of the solid substrate after performing step 4 was 2 ul (density: 10 U/ul) of endonuclease V which specifically digests the mismatched sequence. The temperature of 37° C. was then maintained for about 1 hour to produce the nucleic acid fragment-bonded bead as an enzyme reaction product.

f. Step 6: Observation of the Change of Current During the Translocation of the Enzyme Reaction Product Through Nanopores The change of current was observed during the translocation of the fluid product obtained in step 5, i.e. the enzyme reaction product through nanopores. When a voltage of 300 mV was applied to the nanopore detection unit, the change of current amplitude is shown in FIG. 5. The current amplitude at that time was 350 pA or less and the dwell time was 2 ms or less.

In view of the observation in FIG. 5, even in case where the PCR product containing the short DNA fragment with a length of 1 kbps or less, particularly 70 bps is used as the sample, the DNA fragment-bonded bead is contained in the final product, i.e., enzyme reaction product, obtained from the method of the present invention described above with the bead-bonded nucleic acid probe fixed to the surroundings of nanopores, and the bead not DNA fragment is detected by the nanopore detection unit. Therefore, it can be seen that a very small-sized DNA fragment can be also readily detected by the nanopore detection unit containing nanopores with the diameter of 100 nm.

Comparative Example

Figure 6:
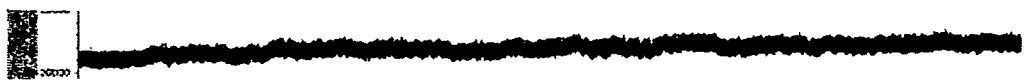
FIG. 6 provides a waveform diagram of current measured after carrying out the steps of FIG. 3 with the apparatus of FIG. 4, using as a target material the 16s RNAs obtained from four kinds of bacteria which are not hybridized with the nucleic acid probe shown in FIG. 3, followed by particularly applying a voltage of 300 mV to the nanopore detection unit.
Figure 6:
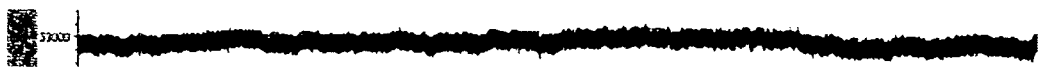
Figure 6:
Figure 6:
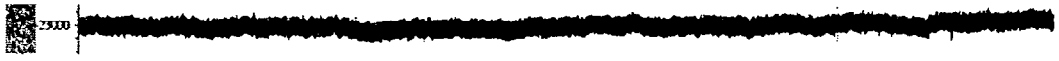

PCR products of 16s RNA from four kinds of bacteria (*Streptococcus pneumoniae, Bordetella pertusis, Staphylococcus aureus, Klebsiella pneumoniae*), which are not hybridized with the nucleic acid probes fixed to the surroundings of nanopores of the solid substrate, were used as a control. The respective steps were carried out under the same condition as that given in the above Example except that the above 16s RNAs were used as a target. After performing the steps, the change of current amplitude obtained from the nanopore detection unit is shown in FIG. 6. As shown in FIG. 6, since control targets were not hybridized with the nucleic acid probes fixed to the surroundings of nanopores, the targets could not also be recognized by an enzyme that specifically digests the mismatched sequence. Therefore, it could be seen that the oligonucleotides attached to the bead were not digested and thus the change of the current amplitude was not also measured in the nanopore detection unit.

According to the nucleic acid detecting method and apparatus using bead and nanopore of the present invention as described above, there are the flowing advantages.

The present invention can detect nucleic acid in a sample to a high-sensitivity by allowing the bead attached to the nucleic acid not the nucleic acid itself to be detected, even in case where the diameter of nanopore in the nanopore detection unit ranges 20 to 120 nm.

And also, the present invention can detect nucleic acid in PCR product to a high-sensitivity using the nanopore detection unit, even in case where the sample to be detected is the PCR product.

Furthermore, the present invention can detect nucleic acid in PCR products to a high-sensitivity using the nanopore detection unit with nanopores of 20 to 120 nm in diameter, even in case where the PCR products as the sample are nucleic acid fragments of 70 to 300 bps in length.

Moreover, the present invention can be implemented on a process-on-a-chip or lab-on-a-chip using microfluidics technology.

While the present invention has been shown and described with respect to particular embodiments, it will be apparent to those skilled in the art that many changes and modifications may be made without departing from the spirit and scope of the invention as defined in the appended claims.

What is claimed is:

1. An apparatus for detecting nucleic acid fragment-bonded beads translocated through nanopores, the apparatus comprising:
    a nanopore detection unit comprising
        (a) a solid substrate having nanopores of the size allowing nucleic acids to be translocated through,
        (b) electrodes applying a voltage to the nanopores of the solid substrate, and
        (c) single stranded nucleic acid probes having a first end attached to the solid substrate in an area surrounding the nanopore and a second end to which beads are attached, wherein each single stranded nucleic acid probe has an artificial sequence cleavable by a specific enzyme within the sequence complementary to a target nucleic acid, and wherein the beads have a diameter from 1 nm to 10 nm in size and are translocatable through nanopore;
    a sample storage chamber for storing the sample containing the target nucleic acids to be added to the nanopore detection unit; and
    an enzyme storage chamber for keeping the specific enzyme to be added to the nanopore detection unit.

2. The apparatus of claim 1, further comprising a connection part for joining each of the sample storage chamber and the enzyme storage chamber to the nanopore detection unit.

3. The apparatus of claim 1, wherein the nanopores have a diameter ranging from 20 nm to 120 nm.

4. The apparatus of claim 1, wherein the artificial sequence cleavable by the specific enzyme has 1 to 3 bases which are mismatched with the target nucleic acid.

5. The apparatus of claim 4, wherein the specific enzyme is a mismatch cleavage enzyme.

6. The apparatus of claim 1, wherein the target nucleic acid has a length ranging from 70 bps to 300 bps.

* * * * *